United States Patent [19]

Cale, Jr. et al.

[11] 4,279,822

[45] Jul. 21, 1981

[54] N-(1-SUBSTITUTED-3-PYRROLIDINYL)-BENZAMIDES

[75] Inventors: Albert D. Cale, Jr., Mechanicsville; Charles A. Leonard, Richmond, both of Va.

[73] Assignee: A. H. Robins Company, Inc., Richmond, Va.

[21] Appl. No.: 747,762

[22] Filed: Dec. 6, 1976

Related U.S. Application Data

[63] Continuation of Ser. No. 658,990, Feb. 18, 1976, abandoned, which is a continuation-in-part of Ser. No. 518,125, Oct. 25, 1974, abandoned, which is a continuation of Ser. No. 340,417, Mar. 12, 1973, abandoned, which is a continuation-in-part of Ser. No. 240,840, Apr. 30, 1972, abandoned.

[51] Int. Cl.$^3$ .................. C07D 207/14; A61K 31/40
[52] U.S. Cl. .............................. 260/326.47; 424/274
[58] Field of Search ..................... 260/326.47

[56] References Cited

U.S. PATENT DOCUMENTS

| | | | |
|---|---|---|---|
| 3,342,826 | 9/1967 | Miller et al. | 260/239 BF |
| 3,577,440 | 5/1971 | Lunsford et al. | 260/326.47 |
| 4,002,757 | 1/1977 | Cale, Jr. | 260/326.47 |
| 4,013,670 | 3/1977 | Banitt et al. | 260/326.47 |

Primary Examiner—Mark L. Berch

[57] ABSTRACT

N-(1-Substituted-3-pyrrolidinyl)benzamides of the formula

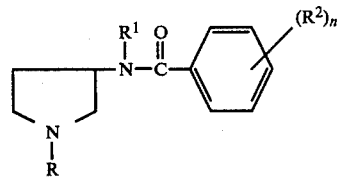

wherein R is cycloalkyl or phenyllower-alkyl; $R^1$ is hydrogen or lower alkyl of 1 to 8 carbon atoms; $R^2$ is acetamido, amino, methylamino, dimethylamino, benzyloxy, halogen, lower alkoxy, methylmercapto, nitro, cyano, hydroxy, sulfamoyl, bis(methylsulfonyl)amino, methylsulfonylamino, aminomethyl or acetylaminomethyl and can be the same or different; n is an integer from one to three inclusive with the proviso that when $R^2$ is amino, nitro, halogen or lower alkoxy, n is greater than one, and pharmaceutically acceptable acid addition salts thereof are disclosed.

4 Claims, No Drawings

N-(1-SUBSTITUTED-3-PYRROLIDINYL)BENZAMIDES

This is a continuation of application Ser. No. 658,990, filed Feb. 18, 1976, now abandoned, which is a continuation-in-part application of copending application Ser. No. 518,125, filed Oct. 25, 1974, now abandoned which is a continuation application of application Ser. No. 340,417, filed Mar. 12, 1973, which was a continuation-in-part application of Ser. No. 240,840, filed Apr. 30, 1972, both now abandoned.

The present invention is concerned with heterocyclic compounds useful as antiemetics and is particularly concerned with certain N-(3-pyrrolidinyl)benzamides, compositions thereof and methods for employing the compositions in controlling emesis in warm blooded animals with minimal side effects.

U.S. Pat. No. 3,342,826 discloses benzamido heterocyclic compounds which are alleged to have great potency in antiemetic tests. In one particular embodiment of said patent the heterocyclic moiety is a pyrrolidine ring having lower alkyl and allyl radicals attached to the secondary nitrogen atom of the pyrrolidine ring and lower alkoxy radicals at the ortho position of the benzamido moiety. The compounds possess the undesirable side effect of producing catalepsy at rather low dosages. We have discovered that when the radical attached to the secondary nitrogen atom of the pyrrolidine ring is a cycloalkyl radical such as cyclopentyl, cyclododecyl or cyclohexyl, or a phenylloweralkyl radical, the compounds possess desirable antiemetic properties and furthermore the presence of a lower alkoxy radical at the ortho position of the benzamido moiety is not necessary for antiemetic activity. We have further discovered that when the radical attached to the secondary nitrogen atom of the pyrrolidine ring is cyclohexyl, the antiemetic activity is generally enhanced compared to the prior art compounds and, furthermore, when the amido nitrogen has a lower alkyl substituent, the compounds are free of the undesirable side effects of catalepsy. Thus, the compounds of the present invention which have the combination of a cyclohexyl radical on the secondary nitrogen atom of the pyrrolidine ring and a lower alkyl radical on the amido nitrogen represent a preferred embodiment. We have also discovered that when the preferred compounds are administered to animals in dosages for emesis control, side effects such as behavioral, tranquilizing, depressant, antihistaminic and drug potentiating effects are minimal. Benzamide compounds having analgetic and antidepressant properties are disclosed in U.S. Pat. No. 3,577,440.

The antiemetic compounds of the present invention are benzamides illustrated generally by the following formula:

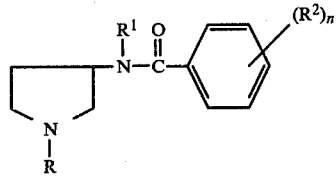

wherein;
R is cycloalkyl or phenyllower-alkyl,
$R^1$ is hydrogen or lower-alkyl of 1 to 8 carbons,
$R^2$ is acetamido, amino, methylamino, dimethylamino, benzyloxy, lower alkoxy, halogen, methylmercapto, nitro, cyano, hydroxy, sulfamoyl, bis(-methylsulfonyl)amino, methylsulfonylamino, aminomethyl or acetylaminomethyl and can be the same or different,
n is an integer from one to three inclusive with the proviso that when $R^2$ is amino, nitro, halogen or lower alkoxy, n is greater than one, and
pharmaceutically acceptable acid addition salts thereof.

The nontoxic pharmaceutically acceptable acid addition salts of the basic compounds of Formula I are also included within the scope of this invention, since such salts can likewise be used as antiemetics. Both organic an inorganic acids can be employed to form the pharmaceutically acceptable acid addition salts, illustrative acids being sulfuric, nitric, phosphoric, citric, acetic, lactic, tartaric, sulfamic, succinic, fumaric, maleic, hydrochloric, hydrobromic, benzoic, and the like. The salts are prepared by methods well known to the art.

It is, therefore, an object of the present invention to provide novel N-(1-substituted-3-pyrrolidinyl)benzamides and a method for controlling emesis. Another object is to provide a method for controlling emesis with minimal side effects. A still further object is to provide novel compositions useful as antiemetics.

Additional objects and advantages of the present invention will be apparent to one skilled in the art and still others will become apparent from the following description of the best mode of carrying out the present invention and from the appended claims.

In the definition of the symbols in Formula I given above, and where they appear elsewhere throughout the claims and specification hereof, the terms have the following significance.

The term "cycloalkyl" as used herein includes primarily cyclic alkyl radicals containing four up to twelve carbon atoms inclusive and includes such groups as cyclobutyl, cyclopentyl, cyclohexyl, cycloheptyl and the like.

The term "halogen" includes fluorine, chlorine, bromine and iodine.

The term "lower-alkyl" includes straight and branched chain radicals containing 1 to 8 carbon atoms as, for example, methyl, ethyl, propyl, isopropyl, n-butyl, isobutyl, tertiary butyl, amyl, isoamyl, n-hexyl, n-heptyl, and n-octyl radicals. Lower-alkoxy has the formula -O-lower-alkyl.

Included in the term "phenyllower-alkyl" are such groups as benzyl, phenethyl and the like.

METHOD OF PREPARATION

The preparation of the benzamido compounds of Formula I may be accomplished by mixing and reacting the appropriately substituted 3-aminopyrrolidine (II) with a substituted benzoyl chloride (III) or an equivalent thereof (e.g., a benzoylazide) according to the reaction sequence:

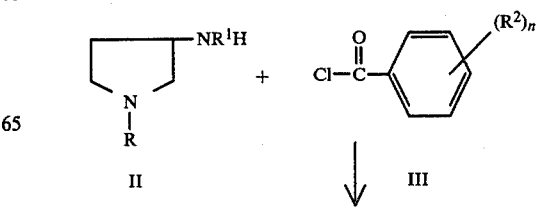

-continued

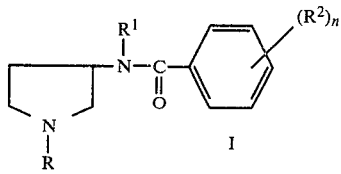

wherein R, $R^1$, $R^2$ and n are as defined above except that $R^2$ cannot be primary amino, hydroxy or acetamido.

Compounds of Formula I wherein $R^2$ is primary amino or acetamido are prepared by catalytic hydrogenation of a precursor nitro compound to give an amino compound and acylation of the latter to give an acetamido compound.

Compounds of Formula I wherein $R^2$ is hydroxy are prepared by catalytic hydrogenoylsis of a precursor compound wherein $R^2$ is benzyloxy.

The 3-aminopyrrolidine starting materials (II) are prepared by the procedures disclosed in U.S. Pat. No. 3,337,580. The substituted benzoyl chlorides (III) are either known compounds or they can be prepared by procedures well known to the art.

EXAMPLE 1

4-Amino-N-(1-cyclohexyl-3-pyrrolidinyl-N-methylbenzamide Cyclohexanesulfamate.

4-Nitro-N-(1-cyclohexyl-3-pyrrolidinyl)-N-methylbenzamide was prepared from 15 g. (0.085 mole) of 1-cyclohexyl-3-methylaminopyrrolidine and 15 g. (0.08 mole) p-nitrobenzoyl chloride. The 4-nitro-N-(1-cyclohexyl-3-pyrrolidinyl)-N-methylbenzamide was converted to the fumarate salt (8.4 g., 24%) by precipitation with fumaric acid from isopropanol-isopropyl ether. The fumarate salt was dissolved in 95% ethanol and hydrogenated at three atmospheres of hydrogen over Raney Nickel for about two hours. The mixture was filtered, the filtrate concentrated and the residue partitioned between dilute sodium hydroxide and chloroform. The chloroform layer was dried and concentrated and the residue treated with hexamic acid in isopropanol-isopropyl ether. Recrystallization from the same solvent gave 5.2 g. (13.5% overall) of the salt melting 196°-199° C.
Analysis: Calculated for $C_{24}H_{40}N_4O_4S$: C,59.97; H,8.39; N,11.66. Found: C,59.84; H,8.39; N,11.55.

EXAMPLE 2

N-(1-Benzyl-3-pyrrolidinyl)-3,4,5-trimethoxybenzamide

A mixture of 1.8 g (0.01 mole) of 3-amino-1-benzyl-pyrrolidine, 2.4 g. (0.01 mole) of 3,4,5-trimethoxybenzoyl azide, and 25 ml. of dry benzene was stirred 16 hours at room temperature followed by stirring for one hour at about 60° C. The mixture was cooled and 50 ml. of isopropyl ether added to the mixture. The crude crystalline product was separated by filtration and recrystallized from ethyl acetate-isopropyl ether mixture, giving 2.2 g. (60% yield). The melting point of the product after a second recrystallization from the same solvent was 128°-129° C.
Analysis: Calculated for $C_{21}H_{26}N_2O_4$: C,68.09; H,7.08; N,7.56. Found: C,68.00; H,7.26; N,7.62.

EXAMPLE 3

N-(1-Cyclohexyl-3-pyrrolidinyl)-4-dimethylamino-N-methylbenzamide Fumarate

To 16.5 g. (0.1 mole) of 4-dimethylaminobenzoic acid in 100 ml. of carbon tetrachloride was added dropwise with stirring 37.4 g. (0.11 mole) of trioctylphosphene. After the solution had stirred an additional 15 minutes, 18.5 g. (0.1 mole) of 1-cyclohexyl-3-methylaminopyrrolidine was added with continued stirring. The crystalline product which precipitated after an additional one-hour stirring time was separated by filtration and recrystallized from methyl isobutyl ketone containing a small amount of methanol. The impure material was partitioned between chloroform and dilute sodium hydroxide, the chloroform solution was concentrated and the residue converted to the fumarate salt in a mixture of isopropanol ether-isopropanol. After recrystallizing from isopropanol-methanol, 6.1 g. (14%) product was obtained which melted at 185°-186° C.
Analysis: Calculated for $C_{24}H_{35}N_3O_5$: C,64.70; H,7.92; N,9.43. Found: C,64.29; H,8.00; N,9.43.

EXAMPLE 4

N-(1-Cyclohexyl-3-pyrrolidinyl)-4-acetamidobenzamide

To a suspension of 8.6 g. (0.3 mole) of 4-amino-N-(1-cyclohexyl-3-pyrrolidinyl)benzamide in 50 ml. of chloroform was added dropwise with stirring, 3.37 g. (0.03 mole) of acetic anhydride. The mixture was stirred for 30 minutes and the solution extracted with dilute sodium hydroxide. The chloroform layer was dried over sodium sulfate, filtered and concentrated. The residue was dissolved in hot ethyl acetate and an equivalent amount of isopropyl ether added to precipitate the product. After recrystallizing from the same solvent, 5.1 g. (50%) of product melting at 184°-186° C. was obtained.
Analysis: Calculated for $C_{19}H_{27}N_3O_2$: C,69.27; H,8.26; N,12.76 Found: C,69.22; H,8.28; N,12.70

EXAMPLE 5

4-Methylamino-N-(1-cyclohexyl-3-pyrrolidinyl)-N-methylbenzamide Dihydrochloride

A solution of 50 ml. of thionyl chloride and 16 g. (0.065 mole) of p-(N-methyltrifluoroacetamido)benzoic acid was refluxed for 2.5 hours. The solution was concentrated under reduced pressure and the residue dissolved in 50 ml. of chloroform. After removing the chloroform under reduced pressure the residue was again dissolved in 50 ml. of chloroform and to the solution was added 13 g. (0.071 mole) of 1-cyclohexyl-3-methylaminopyrrolidine. The solution was stirred 15 minutes and washed with dilute sodium hydroxide. After evaporation of the chloroform, the residue was dissolved in 400 ml. of 3 N hydrochloride acid by heating on a steam bath for 30 minutes. The acid solution was basified with aqueous sodium hydroxide and extracted with chloroform. The extract was concentrated and the residue chromatographed on a magnesium silicate column eluting with benzene and acetone in one liter portions of % benzene/% acetone of 100/0; 99:1; 98:2; 96/4; 92/8; 84/16; 68/32; 34/66; 0/100 followed by several liters of acetone. The eluant was collected in 500 ml. fractions, fractions 18 to 24 being combined and concentrated under reduced pressure. Nuclear magnetic resonance and mass spectrum analyses indicated that the residue was the titled compound. A small portion was distilled in a molecular still.

Analysis: Calculated for $C_{19}H_{29}N_3O$: C,72.34; H,9.27; N,13.32. Found: C,72.07; H,9.22; N,12.93.

The remainder of the free base was converted to the dihydrochloride salt with ethereal hydrogen chloride in methylisobutyl ketone-ethanol. Melting point of the salt was about 205° C.

EXAMPLE 6

N-(1-Cyclohexyl-3-pyrrolidinyl)-3,5-dinitrobenzamide

To 8.0 g. (0.05 mole) of 3-amino-1-cyclohexylpyrrolidine in chloroform was added with stirring 12 g. (0.052 mole) of 3,5-dinitrobenzoylchloride. After stirring one hour, the solution was extracted with dilute sodium hydroxide, dried over sodium sulfate and concentrated. The residue was recrystallized from isooctane-ethyl acetate. The product weighed 5.1 g. (29%) and melted at 159°–161° C.

Analysis: Calculated for $C_{17}H_{22}N_2O_5$: C,56.35; H,6.12; N,15.46. Found: C,56.17; H,6.13; N,15.51.

EXAMPLE 7

N-(1-Cyclohexyl-3-pyrrolidinyl)-3,5-diaminobenzamide

When in the procedure of Example 1, N-(1-cyclohexyl-3-pyrrolidinyl)-3,5-dinitrobenzamide is used in place of 4-nitro-N-(1-cyclohexyl-3-pyrrolidinyl)-N-methylbenzamide there is obtained N-(1-cyclohexyl-3-pyrrolidinyl)-3,5-diaminobenzamide.

EXAMPLE 8

N-(1-Cyclohexyl-3-pyrrolidinyl)-4-[bis(methylsulfonyl)amino]benzamide

To a stirring solution of 4-amino-N-(1-cyclohexyl-3-pyrrolidinyl)benzamide monohydrate (15.0 g.; 0.05 mole) in 100 ml. of chloroform maintained at room temperature was added dropwise 11.4 g. (0.10 mole) of methanesulfonyl chloride. Stirring was continued at room temperature for two hours and then an equivalent of sodium carbonate in 75 ml. of water was added with stirring continued overnight. The chloroform layer was washed successively with dilute hydrochloric acid and dilute sodium hydroxide solution, dried over sodium sulfate and concentrated at reduced pressure. The residue after two crystallizations from ethyl acetate containing a small amount of isopropanol weighed 3.5 g. (19% yield) and melted at 176°–178° C.

Analysis: Calculated for $C_{19}H_{29}N_3O_5S_2$: C,51.45; H,6.59; N,9.48. Found: C,51.69; H,6.72; N,9.37.

EXAMPLE 9

4-Aminomethyl-N-(1-cyclohexyl-3-pyrrolidinyl)benzamide

A solution of 20 g. (0.067 mole) of 4-cyano-N-(1-cyclohexyl-3-pyrrolidinyl)benzamide in 400 ml. of 95% ethanol and 19.24 g. (0.202 mole) of concentrated hydrochloric acid containing 2.0 g. of palladium on charcoal (10%) was shaken at room temperature in three atmospheres of hydrogen for five hours. The filtered mixture was concentrated at reduced pressure and the residue was partitioned between dilute sodium hydroxide and chloroform. The dried chloroform solution was concentrated at reduced pressure and the residue was recrystallized from ethyl acetate to give 8.0 g. (40%) of product which melted at 125°–129° C.

Analysis: Calculated for $C_{18}H_{27}N_3O$: C,71.72; H,9.03; N,13.94. Found: C,71.61; H,9.02; N,13.62.

The physical constants of some representative N-1-substituted-3-pyrrolidinyl)benzamides made by the procedures generally disclosed hereinabove and described in detail in Examples 1–9 are set forth in Table I and Table II.

TABLE I

Examples 10–36

| Example | R | $R^1$ | $(R^2)_n$ | M.P. (B.P.)°C. | Salt |
|---|---|---|---|---|---|
| 10 | $C_5H_{11}$ | H | 3,4-$Cl_2$ | 134–6 | — |
| 11 | $C_6H_{11}$ | H | 3,4-$(C_2H_5O)_2$ | 151–2 | — |
| 12 | $C_6H_{11}$ | H | 3,4,5-$(CH_3O)_3$ | 142–5 | — |
| 13 | $C_6H_{11}$ | $CH_3$ | 2,4-$(CH_3O)_2$ | (265–75: 4 mm) | — |
| 14 | $C_6H_{11}$ | H | 2,4-$Cl_2$ | 122–4 | — |
| 15 | $C_6H_{11}$ | H | 4-$SCH_3$ | 120–3 | — |
| 16 | $C_6H_{11}$ | H | 2,4-$(CH_3O)_2$ | 186–8 | fumarate |
| 17 | $C_6H_{11}$ | H | 4-$N(CH_3O)_2$ | 138–41 | — |
| 18 | $C_6H_{11}$ | H | 2-$CH_3O$, 4-$NH_2$, 5-Cl | 113–15 | fumarate |
| 19 | $C_6H_{11}$ | $CH_3$ | 2,4-$(NO_2)_2$ | 245–7 | hydrochloride |
| 20 | $C_6H_{11}$ | H | 2-$CH_3O$, 5-$SONH_2$ | 184–7 | — |
| 21 | $C_6H_{11}$ | $CH_3$ | 3,5-$(NO_2)_2$ | 228–31 (dec.) | hydrochloride |
| 22 | $C_6H_{11}$ | $CH_3$ | 3,4-$(C_2H_5O)_2$ | 179–81 | hydrochloride |
| 23 | $C_6H_{11}$ | $CH_3$ | 4-$SCH_3$ | 196–8 | hydrochloride |
| 24 | $C_6H_{11}$ | H | 3-$C_6H_5CH_2O$ | 119–20 | — |
| 25 | $C_6H_{11}$ | H | 3-OH | 210–11 | — |
| 26 | $C_6H_{11}$ | $CH_3$ | 3-OH | 130–2 | — |
| 27 | $C_6H_{11}$ | H | 4-CN | 198–200 | hydrochloride |
| 28 | $C_6H_{11}$ | $CH_3$ | 4-CN | 194–5 | hydrochloride |
| 29 | $C_6H_{11}$ | $CH_3$ | 2-$CH_3O$, 4-$NH_2$, 5-Cl | 195–8 | disulfate hydrate |
| 30 | $C_5H_9$ | $CH_3$ | 4-$NH_2$ | 179–80 | cyclohexanesulfamate |
| 31 | $C_{12}H_{23}$ | $CH_3$ | 4-$NH_2$ | 123–5 | — |
| 32 | $C_6H_{11}$ | $CH_3$ | 4-$CH_3CONH$ | 179–84 | fumarate |
| 33 | $C_6H_{11}$ | H | 3-$CH_3CONH$ | 148–50 | — |
| 34 | $C_6H_{11}$ | H | 4-$CH_3SO_2NH$ | 212–3 | — |
| 35 | $C_6H_{11}$ | H | 2-$CH_3CONH$ | 184–5 | fumarate |
| 36 | $C_6H_5CH_2$ | H | 4-$CH_3CONH$ | 138–40 | — |

TABLE II

Analytical Data - Examples 10–36

| Example | Empirical Formula | Calculated C | Calculated H | Calculated N | Found C | Found H | Found N |
|---|---|---|---|---|---|---|---|
| 10 | $C_{17}H_{22}Cl_2N_2O$ | 59.83 | 6.50 | 8.21 | 59.71 | 6.54 | 8.15 |
| 11 | $C_{21}H_{32}N_2O_3$ | 69.97 | 8.95 | 7.77 | 69.70 | 8.95 | 7.73 |
| 12 | $C_{20}H_{30}N_2O_4$ | 66.27 | 8.34 | 7.73 | 66.28 | 8.48 | 7.87 |
| 13 | $C_{20}H_{30}N_2O_3$ | 69.33 | 8.73 | 8.09 | 69.40 | 8.81 | 7.95 |
| 14 | $C_{17}H_{22}N_2Cl_2O$ | 59.83 | 6.50 | 8.21 | 59.67 | 6.57 | 8.18 |
| 15 | $C_{18}H_{26}N_2OS$ | 67.88 | 8.23 | 8.80 | 67.39 | 8.20 | 8.74 |
| 16 | $C_{23}H_{32}N_2O_7$ | 61.59 | 7.19 | 6.25 | 61.18 | 7.15 | 6.19 |
| 17 | $C_{19}H_{29}N_3O$ | 72.34 | 9.27 | 13.32 | 71.88 | 9.29 | 12.90 |
| 18 | $C_{22}H_{30}ClN_3O_5$ | 56.47 | 6.46 | 8.90 | 55.89 | 6.44 | 8.89 |
| 19 | $C_{18}H_{25}ClN_4O_5$ | 52.36 | 6.10 | 13.57 | 52.39 | 6.13 | 13.50 |
| 20 | $C_{18}H_{27}N_3O_4S$ | 56.67 | 7.13 | 11.02 | 56.39 | 7.09 | 11.00 |
| 21 | $C_{18}H_{25}ClN_4O_5$ | 52.36 | 6.10 | 13.57 | 52.08 | 6.16 | 13.39 |
| 22 | $C_{22}H_{35}ClN_2O_3$ | 64.30 | 8.58 | 6.82 | 64.24 | 8.54 | 6.72 |
| 23 | $C_{19}H_{29}ClN_2OS$ | 61.85 | 7.92 | 7.59 | 61.69 | 7.89 | 7.48 |

TABLE II-continued

Analytical Data - Examples 10-36

| Example | Empirical Formula | Calculated C | Calculated H | Calculated N | Found C | Found H | Found N |
|---|---|---|---|---|---|---|---|
| 24 | $C_{24}H_{30}N_2O_2$ | 76.16 | 7.99 | 7.40 | 75.87 | 8.09 | 7.28 |
| 25 | $C_{17}H_{24}N_2O_2$ | 70.80 | 8.39 | 9.71 | 70.50 | 8.24 | 9.53 |
| 26 | $C_{18}H_{26}N_2O_2$ | 71.49 | 8.67 | 9.26 | 71.23 | 8.67 | 9.26 |
| 27 | $C_{18}H_{24}ClNO_3$ | 64.76 | 7.25 | 12.59 | 64.78 | 7.35 | 12.56 |
| 28 | $C_{19}H_{26}ClNO_3$ | 65.60 | 7.53 | 12.08 | 65.20 | 7.55 | 12.03 |
| 29 | $C_{19}H_{34}ClN_3O_{11}S$ | 39.34 | 5.91 | 7.24 | 39.52 | 5.71 | 6.82 |
| 30 | $C_{23}H_{38}N_4O_4S$ | 59.20 | 8.21 | 12.01 | 58.93 | 8.20 | 12.06 |
| 31 | $C_{24}H_{30}N_3O$ | 74.76 | 10.20 | 10.90 | 74.77 | 10.28 | 10.81 |
| 32 | $C_{24}H_{33}N_3O_6$ | 62.73 | 7.24 | 9.14 | 62.48 | 7.17 | 9.14 |
| 33 | $C_{19}H_{27}N_3O_2$ | 69.27 | 8.26 | 12.76 | 69.01 | 8.14 | 12.77 |
| 34 | $C_{18}H_{27}N_3O_3S$ | 59.15 | 7.45 | 11.50 | 59.56 | 7.42 | 11.47 |
| 35 | $C_{23}H_{31}N_3O_6$ | 62.01 | 7.01 | 9.43 | 62.00 | 7.00 | 9.37 |
| 36 | $C_{20}H_{23}N_3O_2$ | 71.19 | 6.87 | 12.45 | 70.89 | 6.87 | 12.42 |

PHARMACOLOGY

The anti-emetic properties of the compounds of Formula I were established using a modification of the methods of Chen and Ensor, J. Pharmac. Exp. Ther. 98: 245–250 (1950) and of Leonard et al., J. Pharmac. Exp. Ther. 154: 339–345 (1966). Drug activity was assessed by its ability to reduce the frequency of apomorphine-induced emesis in dogs. The dogs were prescreened for fairly constant emetic responses to the subcutaneous administration of 0.1 mg/kg. of apomorphine hydrochloride, and those which vomited five or more times in the 40-minute period after apomorphine administration were selected for drug studies.

Groups of three dogs were used in preliminary tests and for the determinations of time of peak drug effect. Dose response curves were usually obtained using four drug-treated groups; each group contained at least three dogs. The dogs were fed approximately 17 hours prior to a test. Drugs were administered and at suitable intervals the dogs received 0.1 mg/kg of apomorphine hydrochloride subcutaneously. Frequency of emesis was determined during the next 40 minutes and emesis was counted as the actual expulsion of stomach contents.

In oral studies, drugs were administered in gelatin capsules (controls received an empty capsule). In the subcutaneous studies, drugs were administered in distilled water and/or polyethylene glycol-300.

Dogs were re-used at intervals of not less than one week. The $ED_{50}$ is the dose which reduces the frequency of emesis of drug treated dogs to a value 50% below that of controls. Mean frequency of emesis for each drug treated group was compared with a mean control value derived by pooling the prior control emetic frequencies for all dogs used on that test day. The difference is expressed as a percentage decrease relative to controls. The percent decrease in mean frequency of emesis for each drug-treated group (ordinate) was plotted against log dose (abscissa) on semi-log graph sheets. The $ED_{50}$ was calculated by the method of Goldstein (Biostatistics, An Introductory Test; Pages 156–161; The MacMillan Co., New York, 1964).

TABLE III

Anti-Emetic Effect of Subcutaneous Administration (doses expressed as free base)

| Example | $ED_{50}$, mg/kg. |
|---|---|
| 3 | 1.10 |
| 4 | 2.40 |
| 5 | 0.05 |
| 6 | 0.15 |
| 10 | 0.28 |
| 11 | 0.66 |
| 12 | 0.40 |
| 14 | 2.40 |
| 15 | 0.88 |
| 16 | 0.026 |
| 17 | 0.89 |
| 18 | 0.003 |

Table IV sets forth pharmacological data for additional examples expressed as percent reduction in emesis over that of controls. The compounds were administered at dose levels of 5 mg/kg s.c.

TABLE IV

| Example | % Reduction in Emesis |
|---|---|
| 8 | −44 |
| 33 | −87 |
| 34 | −86 |
| 35 | −95 |
| 36 | −59 |

The pharmaceutical compositions of this invention comprise compounds of Formula I in an amount to provide anti-emetic action. The compositions contain 1.0 mg. to 100 mg. active medicament per unit dose. Preferably, the compositions contain from about 5 mg. to about 50 mg. per unit dose.

The pharmaceutical carrier employed in the composition can be either solid or liquid. Exemplary of solid carriers are lactose, magnesium stearate, terra alba, sucrose, talc, stearic acid, gelatin, agar, pectin or acacia. Exemplary of liquid carriers are vegetable oils and water. Similarly, the carrier or diluent may include a sustained release material such as glyceryl monostearate or glyceryl distearate alone or with a wax.

A wide variety of pharmaceutical forms can be employed by methods well known to the art. Thus, if a solid carrier is used the composition can be tableted or prepared as a powder, a troche, a lozenge or a suppository. Gelatin capsules containing the medicament can also be prepared. If a liquid carrier is used, the composition can be in the form of a soft gelatin capsule, a liquid suspension or a syrup. Parenteral dosage forms are obtained by dissolving a water-soluble salt of the active anti-emetic agent in water or saline solution in a concentration such that 1 cc. of the solution contains from 1.0 mg. to 25 mg. of active anti-emetic agent. The solution can then be filled into single or multiple dose ampules.

We claim:

1. N-(1-cyclohexyl-3-pyrrolidinyl)-4-acetamidobenzamide.
2. N-(1-cyclohexyl-3-pyrrolidinyl)-2-methoxy-5-sulfamoylbenzamide.
3. The fumarate salt of N-(1-cyclohexyl-3-pyrrolidinyl)-2-methoxy-4-amino-5-chlorobenzamide.
4. N-(1-cyclohexyl-3-pyrrolidinyl)-2-methoxy-4-amino-5-chlorobenzamide.

* * * * *